United States Patent [19]
Burbury et al.

[11] Patent Number: 5,469,492
[45] Date of Patent: Nov. 21, 1995

[54] SYSTEMS FOR OPERATING X-RAY EQUIPMENT

[75] Inventors: Robert L. Burbury, Elgin, Ill.; Phillip P. Nuccio, Benton Harbor, Mich.

[73] Assignee: Optima Imaging, Inc., Wheeling, Ill.

[21] Appl. No.: 850,891

[22] Filed: Mar. 13, 1992

[51] Int. Cl.[6] ............................................ H05G 1/06
[52] U.S. Cl. .......................... 378/197; 378/193; 378/167
[58] Field of Search .................................... 378/193, 195, 378/196, 189, 197, 167

[56] References Cited

U.S. PATENT DOCUMENTS

| | | | |
|---|---|---|---|
| 2,582,776 | 1/1952 | Greenberg et al. | 378/197 |
| 2,901,202 | 8/1959 | Stava et al. | 378/197 |
| 3,492,482 | 1/1970 | Forsyth | 378/197 |
| 4,266,139 | 5/1981 | Sportelli et al. | 378/156 |
| 5,023,899 | 6/1991 | Ohlson | 378/196 |

OTHER PUBLICATIONS

Two page photocopy of brochure from North Pacific X Ray Co. in Seattle, Wash., showing Adtek Models FR60 and FR78 Radiographic Tables.

*Primary Examiner*—David P. Porta
*Assistant Examiner*—Don Wong
*Attorney, Agent, or Firm*—Leydig, Voit & Mayer, Ltd.

[57] ABSTRACT

Assemblies for mounting X-ray generating apparatus, and permitting the horizontal and vertical adjustment thereof, are provided, which mounting assemblies comprise (a) a frame comprising a pair of horizontally spaced vertical members and one or more horizontal members extending transversely across the vertical members;

(b) a first carriage extending transversely across the vertical members of the frame;

(c) slidable engaging means for enabling the first carriage to travel vertically up and down in respect to the vertical members of the frame;

(d) a second carriage comprising means for attaching X-ray generating apparatus;

(e) slidable engaging means for enabling the second carriage to travel horizontally from side to side in respect to the first carriage; and (f) removable decorator panels mounted to said frame.

Mounting assemblies which comprise a pivotal rod support for the counterweight to offset the load of the first and second carriages and operating systems which comprise such assemblies and/or lead shielding and decorator panels also are provided.

13 Claims, 3 Drawing Sheets

SYSTEMS FOR OPERATING X-RAY EQUIPMENT

TECHNICAL FIELD

The subject invention is related to systems for operating medical X-ray equipment, such as that which is used, for example, in chiropractic offices. The preliminary form of such an X-ray equipment mounting system was disclosed in Disclosure Document No. 296,464, filed in the United States Patent and Trademark Office on Nov. 22, 1991.

BACKGROUND OF THE INVENTION

Conventional equipment for performing diagnostic X-rays on human patients comprises an X-ray source, usually a combination of an X-ray tube, a collimator, and various control mechanisms. The X-ray source generates and focuses X-rays. The patient is interposed between the X-ray source and an X-ray sensitive film. Typically, the X-ray sensitive film is packaged in a cassette which is insertable into a holder.

The X-ray source and film holder are mounted on stands which allow the X-ray source and film to be manipulated and oriented with respect to patients of differing sizes. An example of such prior art systems is shown in FIG. 1. That type of system includes a pair of tube stands, one stand 10 for mounting an X-ray source 11 and another stand 20 for mounting a film holder 21. More specifically, the X-ray source 11 is mounted on a carriage 12 which is adapted to slide up and down a main column 13. Likewise, the film holder 21 is mounted on a carriage 22 (shown in phantom) which slides up and down a column 23 of the film stand 20. The height of the film and X-ray source 11 can be adjusted by moving the carriages 12 and 22 to the height which is appropriate for a particular patient or a particular exposure.

It also is necessary to adjust the distance between the film and the X-ray source. Thus, the column 13 of the source stand 10 is mounted on a second carriage 14. The carriage 14 slides back and forth on a track 15, and the top of the column 13 travels along a rail 16. In this manner, the entire column 13, along with the X-ray source 11 may be set at the appropriate distance from the film.

Technicians operating X-ray equipment must be protected because excessive exposure to X-rays poses various health risks. Lead shielding is used for this purpose, and typically, it is built into the walls of a room in which the X-ray equipment will be operated. That is, lead shielding customarily is nailed directly to the wall and ceiling studs. Sheet rock, or other types of wall finishing material, is nailed over the lead shielding and the wall is otherwise finished and decorated.

This type of system has been used widely, and tube stands are commercially available from a variety of sources. It has become apparent to applicants, however, that this type of conventional system presents a number of disadvantages.

First, the source stand utilizes a floor track, and the track is mounted on the floor at some distance from the wall, where there is a tendency for technicians and patients to trip over it. The track also can make it more difficult to maneuver a patient gurney into position between the film and X-ray source. Further, the track creates a nuisance to cleaning personnel who are responsible for cleaning or vacuuming the floor, especially the floor between the track and the wall.

Secondly, there is excessive inertia which must be overcome in order to move the X-ray source to the correct distance from the film. That is, the weight of the entire main column as well as the X-ray source is carried on the track of the source stand. Because the track is situated on the floor, it also naturally tends to accumulate dirt and other foreign material, and that may interfere with smooth, easy horizontal movement of the carriage along the track.

It also will be appreciated that installation of this type of system is fairly complicated. The track must be installed separately from the rail, yet both must be properly aligned relative to each other and to the column. Improper alignment of the track or rail can make it difficult or impossible to set the column or for it to be moved easily from side to side.

Additionally, the track must be mounted on the floor, often over a layer of carpet. In many commercial facilities, that involves drilling a hole into a concrete subfloor and setting a screw anchor. Drilling through carpet, however, can cause runs which damage the carpet well beyond the footprint of the track.

Moreover, the manner in which conventional systems are built and installed will increase the cost of locating and relocating the equipment. As noted, lead shielding typically is built into the wall. During a move, the lead shielding must be abandoned, or reclaimed at great expense. Additionally, the carpeting, if any, may require replacement because of holes drilled when originally mounting the floor track.

Finally, floor space often is at a premium, for example if the X-ray equipment is mounted in a vehicle to provide mobile X-ray capabilities. Especially for such mobile applications, any reduction of the floor space which the system occupies offers an advantage.

An object of this invention, therefore, is to provide systems and assemblies for mounting X-ray equipment which allow for vertical and horizontal adjustment of an X-ray source, which are more compact and less intrusive and which do not utilize a floor track.

A further object of the subject invention is to provide such systems and assemblies which allow for horizontal adjustment of the X-ray equipment to be made more easily and reliably.

Another object is to provide such systems and assemblies which are more easily, reliably, and economically installed, and which may be installed without damage to any carpeting which may be present.

Yet another object of the subject invention is to provide systems and assemblies which not only can be installed more easily, but are more easily and economically moved to a new location.

It also is an object of the subject invention to provide systems and assemblies which are more compact, less obtrusive, and occupy less floor space, and/or which otherwise are more compatible with mobile applications.

Another object of the subject invention to provide systems and assemblies wherein all of the above mentioned advantages are realized.

Those and other objects and advantages of the invention will be apparent to those skilled in the art upon reading the following detailed description and upon reference to the drawings.

SUMMARY OF THE INVENTION

Those objects are achieved, in general, by utilizing certain new and useful assemblies for mounting X-ray generating apparatus, by using lead shielding and decorator panels, and by improvements in other aspects of conventional X-ray operating systems. In accordance therewith, the subject invention provides for an assembly for mounting X-ray generating apparatus, and permitting the horizontal and vertical adjustment thereof, which mounting assembly comprises:

(a) a frame comprising a pair of horizontally spaced vertical members and one or more horizontal members extending transversely across the vertical members;

(b) a first carriage extending transversely across the vertical members of the frame;

(c) slidable engaging means for enabling the first carriage to travel vertically up and down in respect to the vertical members of the frame;

(d) a second carriage comprising means for attaching X-ray generating apparatus;

(e) slidable engaging means for enabling the second carriage to travel horizontally from side to side in respect to the first carriage; and, (f) removable decorator panels mounted to said frame.

The invention further provides for such mounting assemblies which comprise a pivotal rod support for the counterweight to offset the load of the first and second carriages and for operating systems which comprise such assemblies and/or lead shielding and decorator panels.

DETAILED DESCRIPTION OF THE INVENTION

Figure 1:
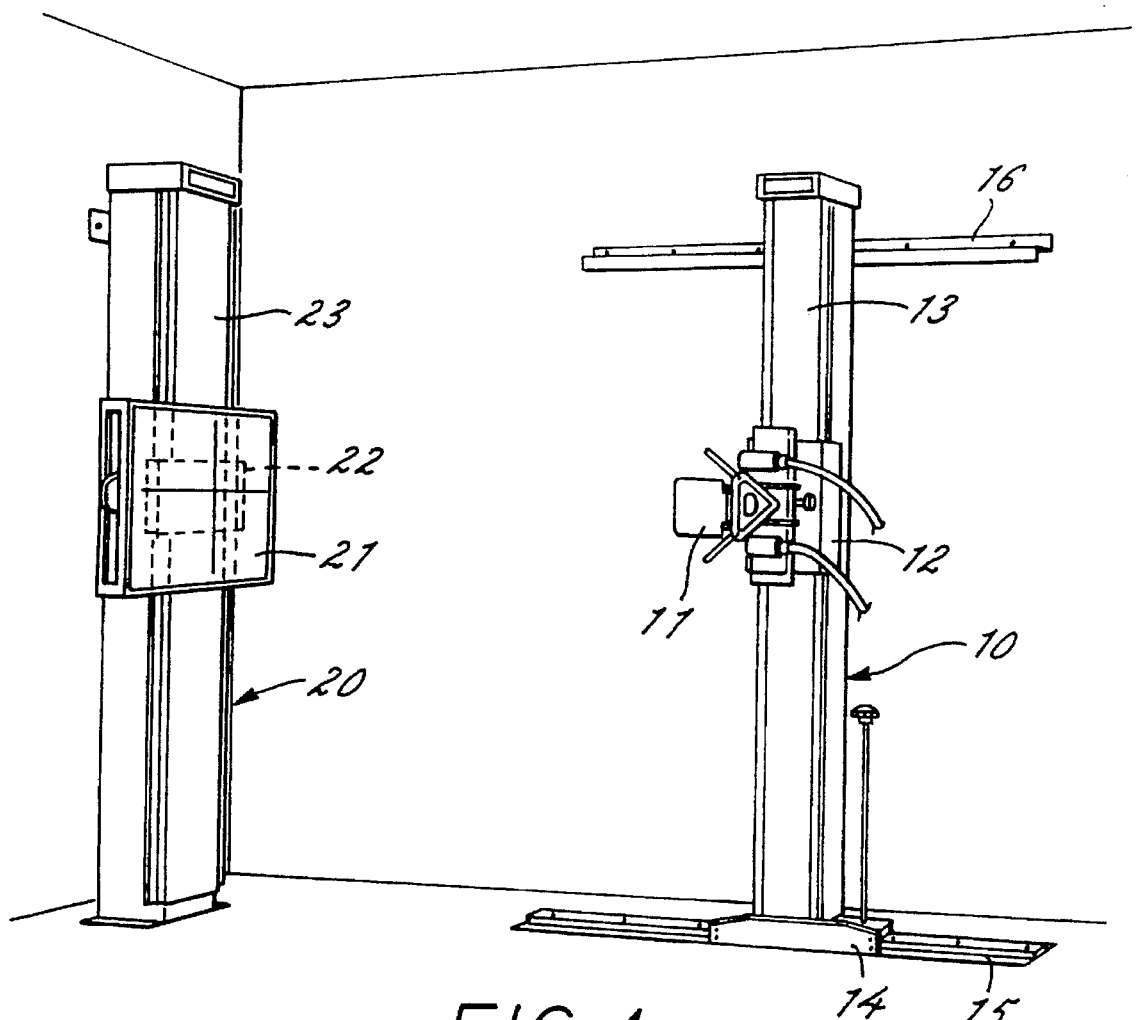
FIG. 1 is a perspective drawing of a prior art system for operating X-ray apparatus showing a stand on which is mounted a film holder, a stand on which is mounted an X-ray generating source, and the environment in which the system is installed.
Figure 2:
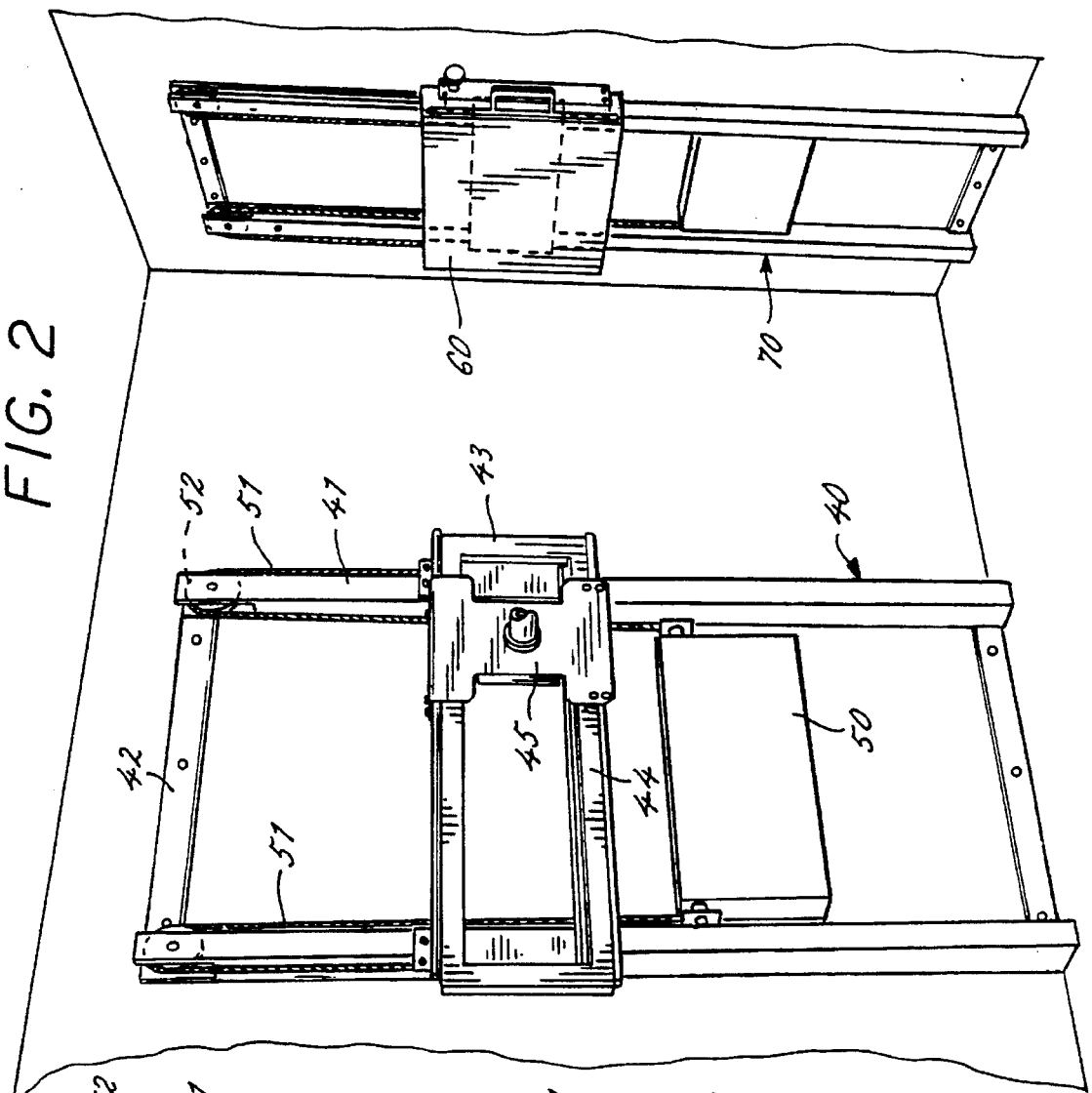
FIG. 2 is a perspective drawing of a preferred embodiment of the operating systems and mounting assemblies of the subject invention showing a film stand, a source stand, and the environment in which the system is used.

As best shown in FIG. 2, a preferred embodiment of the subject invention comprises a system for operating X-ray equipment which generally includes four components: an X-ray source 30, a stand 40 for mounting the X-ray source 30, a holder 60 for X-ray sensitive film, and a stand 70 for mounting the film holder 60. The X-ray source 30 and the film holder 60 may be any of the units commercially available from a number of sources, e.g., the selection of those components is a matter of convenience dictated by factors well known in the art.

Figure 3:
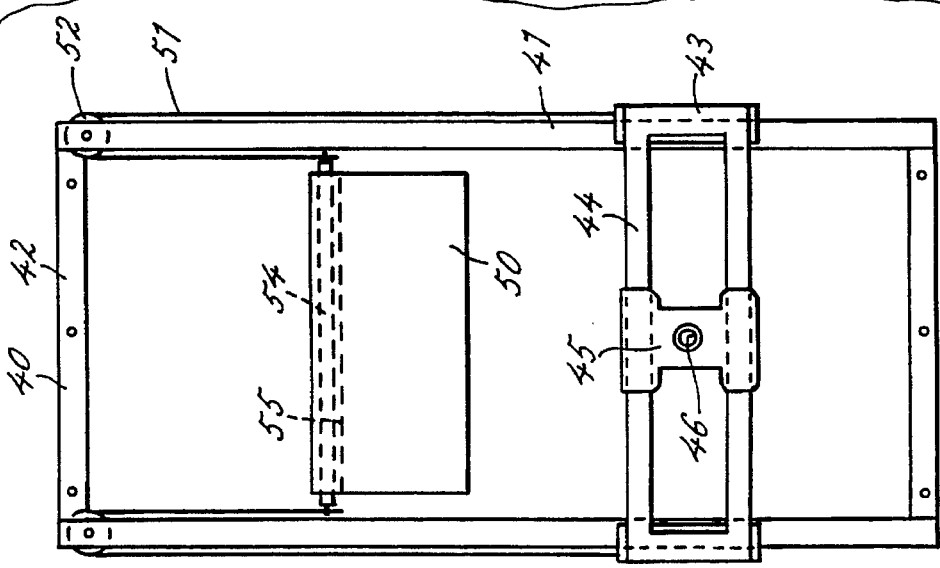
FIG. 3 is a front plan view of the source stand shown in FIG. 2, in which the X-ray generating apparatus is removed.

The source stand 40, as can be seen best in FIG. 3, comprises a frame. In turn, the frame comprises a pair of horizontally spaced vertical members 41 and one or more, in this instance, two horizontal members 42 which extend generally between the vertical members 41.

The source stand 40 also comprises a first carriage 43. The first carriage 43 has a pair of horizontal members 44 extending generally between the vertical members 41, although the two horizontal members 44 could be a single, unitary member if desired.

The vertical members 41 of the frame and the first carriage 43 comprise cooperating means by which the first carriage 43 engages and can slide up and down in respect to the vertical members 41. Such means may include channels in or tracks mounted on (not shown) the vertical members 41 with cooperating projections, bearing surfaces, or rollers (not shown) disposed on the ends of the first carriage 43. The precise manner in which this sliding arrangement is achieved, however, is a matter of convenience and any of the well known designs may be utilized.

The source stand 40 also comprises a second carriage 45. The second carriage 45 comprises means for attaching X-ray generating apparatus, in this instance a hole 46 by which, for example, the X-ray source 30 may be mounted by inserting a threaded shaft (not shown) through the hole 46 and securing it with a nut. The precise manner in which the X-ray source is mounted, however, is a matter of choice.

The horizontal members 44 of the first carriage 43 and the second carriage 45 comprise cooperating means by which the second carriage 45 engages and can slide from side to side in respect to the horizontal members 44 of the first carriage 43. As for the means which enable the first carriage 43 to slide vertically, the sliding engagement of the second carriage 45 with the first carriage 43 may be accomplished by conventional designs.

It will be appreciated, therefore, that the source stand 40 permits the X-ray generating apparatus 30 to be adjusted both vertically and horizontally. Vertical adjustment is accomplished by moving the first carriage 43 up and down the vertical members 41 of the frame, and horizontal adjustment by moving the second carriage 45 from side to side on the first carriage 43. Preferably, the frame also includes means, such as set screws (not shown), whereby the carriages 43 and 45 may be substantially immobilized once the proper adjustment has been made.

It also should be appreciated that the horizontal adjustment of the X-ray source 30 is accomplished without the floor track common in prior art designs, and the problems discussed above which are associated with floor tracks. Further, horizontal adjustment is easier, other factors being equal, with the novel source stand 40. Instead of having to move essentially the entire weight of the stand across a floor track, horizontal adjustment requires movement of only the second carriage 45 and X-ray source 30. Thus, less inertia must be overcome to make horizontal adjustments.

The weight of the first carriage 43, second carriage 45, and X-ray source 30 is significant, and thus, the source stand 40 preferably comprises means whereby this weight may be substantially offset so that it will be easier to vertically adjust the first carriage 43. Springs may be provided for this purpose, or as best shown in FIG. 3, a counterweight 50 may be used. The counterweight 50 is attached to the first carriage 43 by a pair of cables 51 which are threaded over a pair of fixed pulleys 52. The cables 51 are attached at one end to the first carriage 43, and at their other end to a rod 53 (shown in phantom). The rod 53 is mounted to the counterweight 50 by a pin 54 situated near the middle of the rod 53 and the middle of the counterweight 50.

The rod 53 can pivot about the pin 54 thereby allowing the counterweight 50 to self level. Further, the rod may be mounted in a U-shaped channel formed in the top portion of the counterweight 50. This will provide a safety advantage if one cable breaks. That is, if a single cable breaks, the end of the rod 53 attached to the broken cable will pivot downward, but only a short distance, until it butts against the bottom of the channel (shown in phantom) 55. The counterweight 50 will remain attached to the unbroken cable.

This counterweight arrangement, especially with the pin mounted rod, is preferred for the advantages discussed above and for further advantages which will become apparent from the discussion which follows. It will be appreciated, however, that other means for offsetting the weight of the first carriage 43, second carriage 45, and X-ray source 30 may be used.

The stand 70 for mounting the film holder 60 is constructed in much the same manner as the source stand 40. More specifically, the film stand 70 comprises a frame. The frame in turn comprises a pair of horizontally spaced vertical members 71 and one or more, in this instance, two horizontal members 72 which extend generally between the vertical members 71.

The film stand 70 also comprises a carriage 73 (shown in phantom). The carriage 73 extends generally between the vertical members 71.

The vertical members 71 of the film stand frame and the film stand carriage 73 comprise cooperating means by which the carriage 73 engages and can slide up and down in respect to vertical members 71. This may be accomplished by any of the designs used in respect to the source stand 40.

Preferably, the film stand 70 also comprises a counterweight 80, which is connected to the film stand carriage by cables 81, pulleys 82, rod, and pin 84 arranged substantially as shown in respect to the counterweight 50 in the source stand 40, or some other means to offset the weight of the film stand carriage 73 and the film holder 60. Likewise, the film stand 70 preferably comprises means for immobilizing the film stand carriage 73 once it is placed in proper alignment.

The frames of the stands 40 and 70 may be constructed of stainless steel, or other metals or plastics, as in large part can be the various carriages 43, 45, and 73. The choice of materials is largely one of convenience so long as the material is strong enough to support the weights involved and durable enough to withstand frequent adjustments.

Operating systems such as this typically are installed in a room dedicated to performing X-rays. The stands 40 and 70 of the subject invention may be installed easily in such rooms, and holes 47 and 77 are provided in the horizontal frame members 42 and 72 for that purpose. The stands 40 and 70 may be mounted on a wall of the room, e.g., by inserting screws through the holes 47 and 77 or by using other conventional fastening means.

It will be appreciated that when the stands 40 and 70 are installed in that manner, the frames of the stands 40 and 70 are substantially flush against the wall to which it is mounted. As compared to prior art tube stands, especially prior art tube stands for X-ray sources, this minimizes the space between the stands and the wall, which is essentially wasted floor space. Thus, operating systems which utilize one or both stands 40 and 70 are particularly useful where space is at a premium, for example, in mobile applications.

Further it should be apparent that the stands 40 and 70 of the subject invention may be installed more easily than conventional tube stands. There are no separate rails or tracks which must be installed or aligned. The stands 40 and 70 are installed as a unit and all alignment of the carriages 43, 45, and 73 has been made in the factory where it can be accomplished more economically and reliably. Moreover, the counterweights 50 and 80 act as built in plumb bobs and levels by which the stands 40 and 70, with or without any required shimming, may be oriented precisely on the wall.

While the stands 40 and 70 may be used to great advantage in any environment, further advantages can be gained by using them in combination with other preferred features of the subject invention. That is, as best shown in the cutaway portions of FIG. 4, lead shielding 91 preferably is installed on the outside surface of the wall 90, e.g., by tacking or stapling, instead of being interposed between the studs and the wall materials as in conventional facilities. Decorator panels 92 then are mounted on the lead shielding 91 to hide the lead shielding 91 and to provide a neater, more aesthetically pleasing environment. Preferably, decorator panels 92 also are mounted on the stands 40 and 70.

Figure 4:
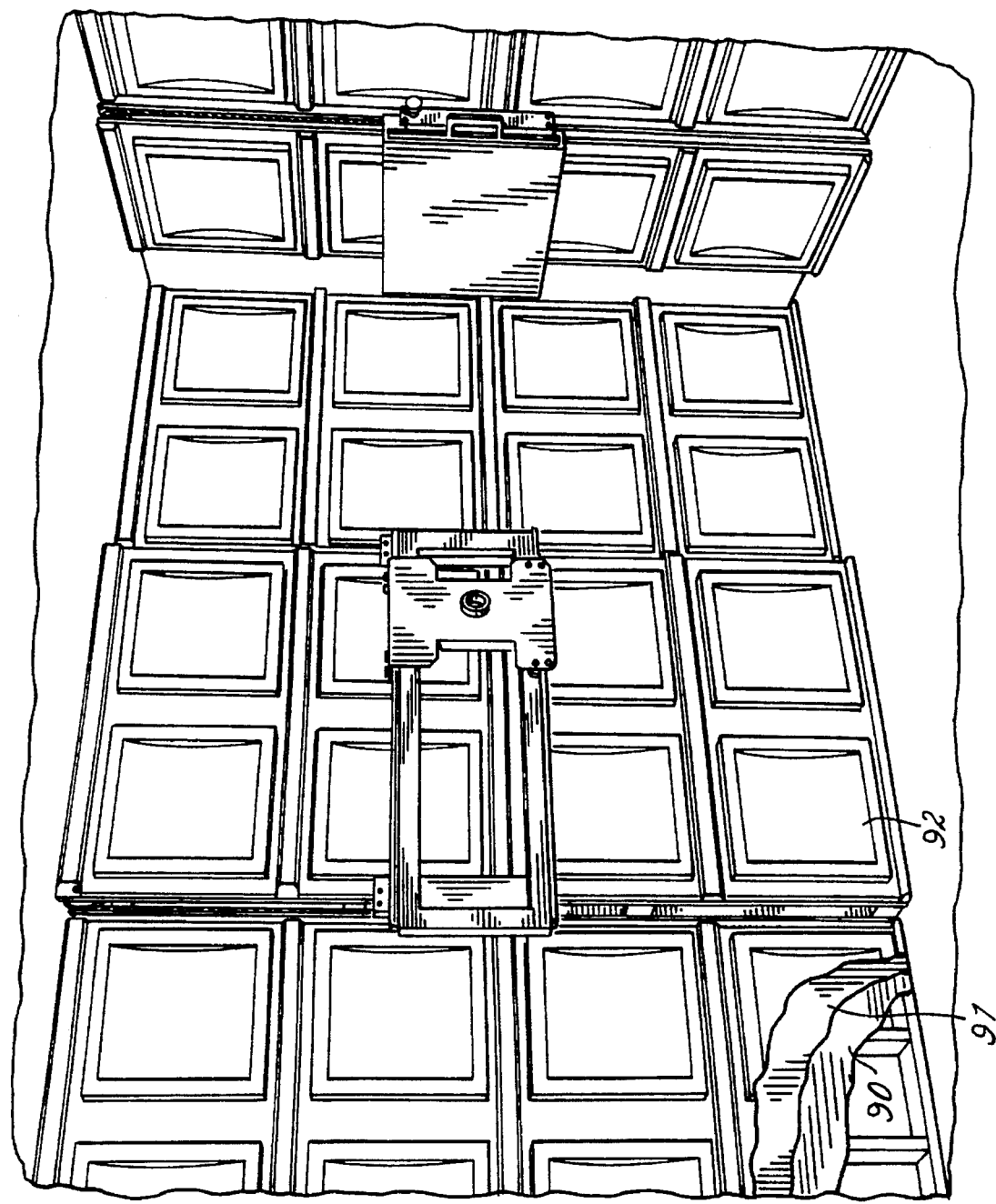
FIG. 4 is substantially the same drawing shown in FIG. 2, except that the use of decorator panels and, by various cut-away portions, lead shielding is shown.

The decorator panels 92 may be made from a molded thermal plastic polymer, as shown in FIG. 4, or in any other shape or from any other material which is aesthetically more pleasing, with or without additional treatment, than is the lead shielding. If desired, such molded panels may incorporate raceways through which wiring may be run. Preferably, they also are dimensioned consistently with other dimensions commonly employed in the construction industry. For example, they may be approximately 2'×2', 2'×4', or 4'×4'.

The panels 91 preferably have interlocking lips (not shown) or other means whereby the seams between the panels 91 may be disguised easily and economically. Any conventional means for affixing the panels 91 over the lead shielding may be used, as appropriate, for example tacking or stapling. Preferably, however, velcro-type fasteners or other means whereby the panels 91 are not damaged during installation or reclamation are preferred.

It will be appreciated that this type of system is easily installed and removed in rooms of conventional construction. The shielding 91 is tacked over a wall 90, and the decorator panels 92 are applied over the shielding 91 and the frames of the stands 40 and 70. If it then is necessary to remove the system, the decorator panels 92 are removed. If a velcro-type fastener has been used, the panels 92 then can be installed in a new location. Likewise, the lead shielding 91 may be salvaged for use in the new location.

While there will be some damage to the wall 90, it ordinarily will consist largely of relatively small holes which can be repaired easily and cheaply. Moreover, because no part of the stands 40 or 70 need be mounted to the floor, any carpet which is present will be undamaged after removal of the stands 40 and 70.

While this invention has been disclosed and discussed primarily in terms of specific embodiments thereof, it is not intended to be limited thereto. Other modifications and embodiments will be apparent to the worker in the art.

We claim:

1. An assembly for mounting a X-ray generating apparatus, and permitting the horizontal and vertical adjustment thereof, which mounting assembly comprises:

(a) a wall mountable frame comprising a pair of horizontally spaced vertical members and one or more horizontal members extending transversely across said vertical members;

(b) a first carriage extending transversely across said vertical members of said frame;

(c) slidable engaging means for enabling said first carriage to travel vertically up and down in respect to said vertical members of said frame;

(d) a second carriage comprising means for attaching X-ray generating apparatus;

(e) slidable engaging means for enabling said second carriage to travel horizontally from side to side in respect to said first carriage;

(f) a counterweight assembly for opposing the weight of said first carriage, the counterweight assembly including cables mounted adjacent each end of the first carriage and a pair of fixed pulleys disposed at a top end of the frame, the cables being looped over the respective pulleys, the counterweight assembly also including a freehanging counterweight suspended from the cables by means of an elongate rod extending between the cables, the rod being pivotably attached to the freehanging counterweight to allow the counterweight to pivot in a vertical plane; and (g) one or more removable decorator panels mounted on said frame.

2. The mounting assembly of claim 1, wherein said frame is adapted to be mounted substantially flush against a wall.

3. A system for operating X-ray apparatus, which system comprises;

(a) apparatus for generating X-rays; said X-ray generating apparatus being mounted on (b) the mounting assembly of claim 2;

(c) a holder for X-ray sensitive film; and said holder being mounted on (d) a stand.

4. The operating system of claim 3, wherein said system comprises;

(e) lead shielding mounted over the outer surface of a wall; and (f) mounted over said lead shielding, one or more decorator panels.

5. A system for operating X-ray apparatus, which system comprises;

(a) apparatus for generating X-rays; said X-ray generating apparatus being mounted on (b) the mounting assembly of claim 1;

(c) a holder for X-ray sensitive film; and said holder being mounted on (d) a stand.

6. The operating system of claim 5, wherein said system comprises;

(e) lead shielding mounted over the outer surface of a wall; and (f) mounted over said lead shielding, one or more decorator panels.

7. The operating system of claim 6, wherein said decorator panels are mounted over said lead shielding by one or more pairs of velcro-type fasteners.

8. The operating system as claimed in claim 6 wherein said decorator panels incorporate raceways for running wiring for said X-ray generating apparatus.

9. The operating systems of claim 5, wherein said stand on which is mounted said film holder comprises;

(i) a frame comprising a pair of horizontally spaced vertical members and one or more horizontal members extending transversely across said vertical members;

(ii) a carriage extending transversely across said vertical members of said film stand frame and comprising means for attaching a film holder; and (iii) slidable engaging means for enabling said film stand carriage to travel vertically up and down in respect to said vertical members of said film stand frame.

10. The operating system of claim 9, wherein said system comprises said one or more decorator panels mounted on said frame of said mounting assembly and on said film stand frame.

11. The operating system as claimed in claim 10 wherein said decorator panels are removably mounted by velcro-type fastening means.

12. In combination with an operating system for X-ray apparatus of the type which comprises apparatus for generating X-rays, a mounting assembly permitting horizontal and vertical adjustment of said X-ray generating apparatus, a holder for X-ray sensitive film, and a stand permitting vertical adjustment of said film holder, the improvement which comprises an assembly for mounting X-ray generating apparatus as set forth in claim 1.

13. An assembly for mounting an X-ray generating apparatus, and permitting the horizontal and vertical adjustment thereof, which mounting assembly comprises:

(a) a wall mountable frame comprising a pair of horizontally spaced vertical members and one or more horizontal members extending transversely across said vertical members;

(b) a first carriage extending transversely across said vertical members of said frame;

(c) slidable engaging means for enabling said first carriage to travel vertically up and down in respect to said vertical members of said frame;

(d) a second carriage comprising means for attaching X-ray generating apparatus;

(e) slidable engaging means for enabling said second carriage to travel horizontally from side to side in respect to said first carriage;

(f) said mounting assembly comprising means for opposing the weight of said first and second carriages, said opposing means including a counterweight; and (g) said counterweight being pivotally mounted to a rod which is suspended by support means attached to the ends of said rod.

* * * * *